United States Patent [19]
Lindgren et al.

[11] Patent Number: 5,395,397
[45] Date of Patent: Mar. 7, 1995

[54] METHOD AND APPARATUS FOR STIMULATING A HEART

[75] Inventors: Anders Lindgren, Taeby; Per Franberg, Stockholm, both of Sweden

[73] Assignee: Siemens Elema AB, Solna, Sweden

[21] Appl. No.: 118,215

[22] Filed: Sep. 9, 1993

[30] Foreign Application Priority Data

Sep. 30, 1992 [SE] Sweden .................. 9202825

[51] Int. Cl.⁶ .................................. A61N 1/368
[52] U.S. Cl. ............................. 607/9; 607/14
[58] Field of Search ..................... 607/9, 14, 25

[56] References Cited

U.S. PATENT DOCUMENTS

| | | |
|---|---|---|
| 4,539,991 | 9/1985 | Boute et al. .................. 607/9 |
| 4,890,617 | 1/1990 | Markowitz et al. . |
| 4,974,589 | 12/1990 | Sholder .................. 607/9 |
| 5,103,820 | 4/1992 | Markowitz . |
| 5,123,412 | 6/1992 | Betzold . |
| 5,129,393 | 7/1992 | Brumwell . |

Primary Examiner—William E. Kamm
Assistant Examiner—Kennedy J. Schaetzle
Attorney, Agent, or Firm—Hill, Steadman & Simpson

[57] ABSTRACT

A heart stimulator is disclosed which is capable of sensing and stimulating both the atrium and ventricle in a heart such a way that a ventricular stimulation pulse is emitted either after a stimulated or spontaneous atrial event following the atrioventricular interval, or after the expiration of a minimum synchronous interval following a stimulated or spontaneous ventricular event, depending on which interval elapses last. The functioning of the heart stimulator, when the atrium's spontaneous rate is faster than a stimulation rate corresponding to the minimum synchronous interval, is improved by delivering an extra atrial stimulation pulse at a second predetermined atrioventricular interval before the next ventricular stimulation pulse, if the interval between the most recently detected atrial event and the next ventricular stimulation pulse exceeds a predetermined threshold value.

16 Claims, 5 Drawing Sheets

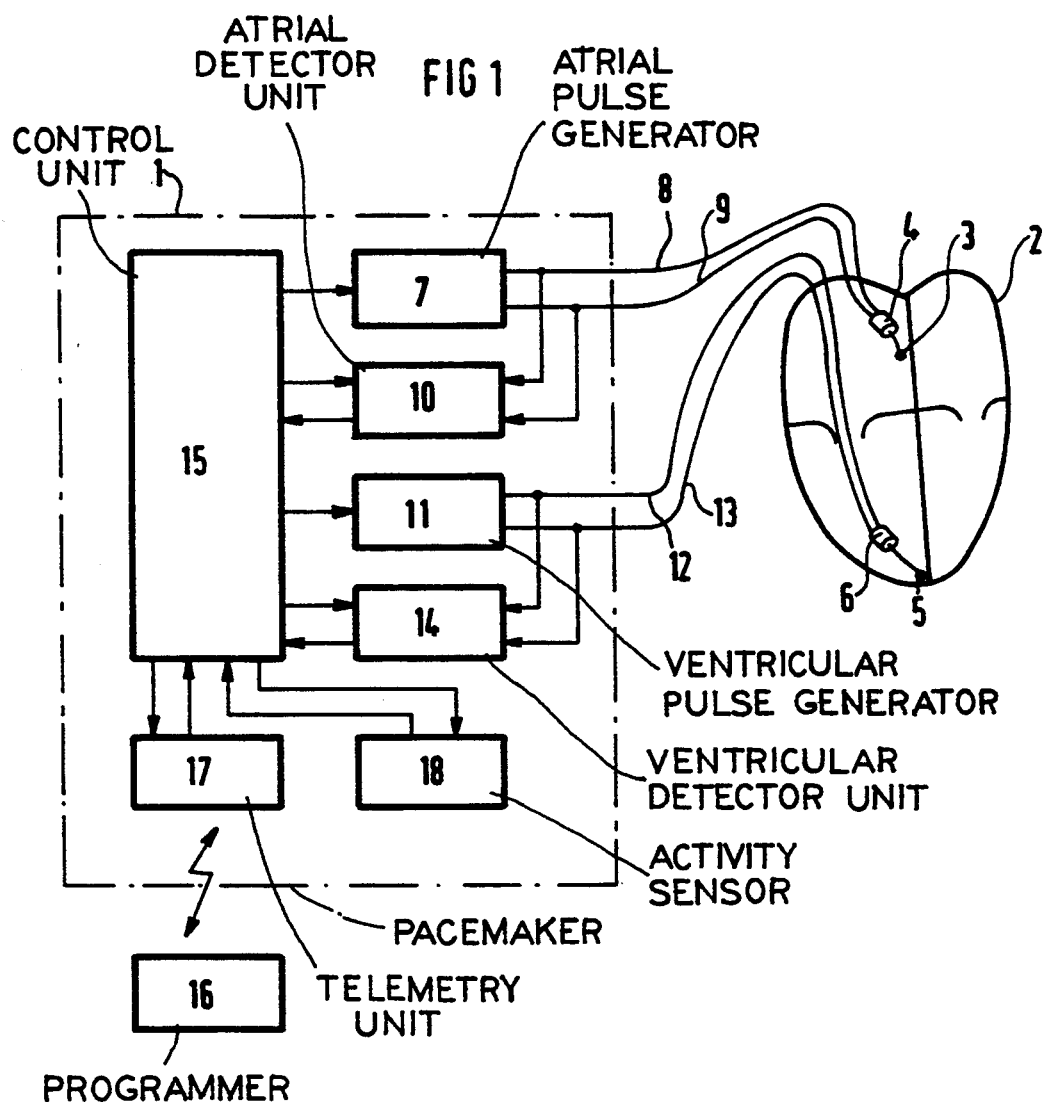

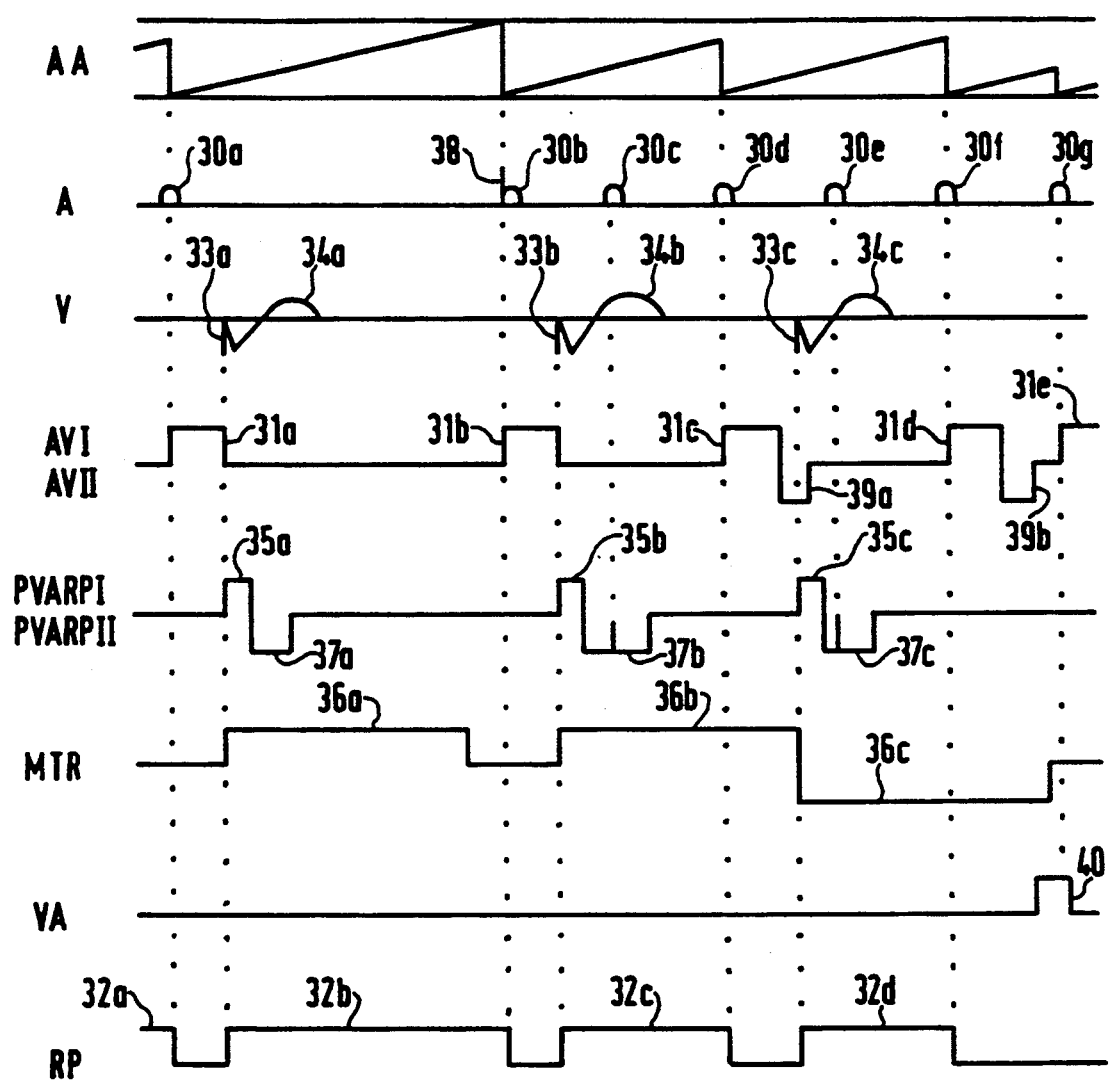

METHOD AND APPARATUS FOR STIMULATING A HEART

BACKGROUND OF THE INVENTION

RELATED APPLICATIONS

This application is related to co-pending application Ser. No. 08/118,214 ("METHOD AND APPARATUS FOR STIMULATING A HEART," A. Lindgren et al.) filed simultaneously herewith and assigned to the same assignee (Siemens AG) as the present application.

FIELD OF THE INVENTION

The present invention relates to methods and devices for stimulating (pacing) a heart, and more particularly to dual chamber pacing devices and methods.

DESCRIPTION OF THE PRIOR ART

Pacemakers are known which include an atrial pulse generator for stimulating atrial events, an atrial detector unit for detecting atrial events, a ventricular pulse generator for stimulating ventricular events, a ventricular detector unit for detecting ventricular events and a control unit for controlling the pulse generators on the basis of the events detected by the detector units. Atrial stimulation pulses are emitted at a programmable basic interval, the next atrial stimulation pulse being inhibited if a spontaneous atrial event is detected. Ventricular stimulation pulses are emitted either after expiration of a first atrioventricular interval following an inhibited stimulation pulse, or a stimulated or spontaneous atrial event or after expiration of a minimum synchronous interval following a stimulated or spontaneous ventricular event, depending on which interval elapses last.

A heart stimulator is described in U.S. Pat. No. 4,890,617 which is designed to sense and stimulate both the atrium and ventricle in a heart. The heart stimulator operates synchronously after spontaneous atrial events by imposing an atrioventricular interval, i.e., an A-V interval, after every detected atrial event. A ventricular stimulation pulse is emitted after the expiration of the A-V interval if no ventricular event was detected in the A-V interval. If the atrium's spontaneous pulse rate slows until the interval between two atrial spontaneous events becomes too long, the heart stimulator takes over and stimulates the atrium at a basic interval, i.e., the A-A interval. After emission of every atrial stimulation pulse, an A-V interval is imposed after whose expiration a ventricular stimulation pulse is emitted. If the spontaneous pulse rate instead increases so that the interval between spontaneous events in the atrium becomes too short, emission of ventricular stimulation pulses is limited by a minimum synchronous interval corresponding to a fastest permissible synchronous stimulation rate. In the event of extensive atrial activity, the heart stimulator will wait for the minimum synchronous interval to expire before emitting a ventricular stimulation pulse. Since the interval elapsing between spontaneous atrial events is shorter than the interval between emitted ventricular stimulation pulses, the interval elapsing between an atrial event and the next ventricular stimulation pulse will increase in each heart cycle. This continues until an atrial event occurs during the atrial refractory period after every emitted ventricular stimulation pulse. The heart stimulator does not interpret atrial events occurring during the refractory period as "approved" atrial events, so the next ventricular stimulation pulse is synchronized with the next atrial event, spontaneous or stimulated. This is known as "Wenckebach blocking". Accordingly, emission of the next ventricular stimulation pulse can occur no later than after expiration of the basic interval, A-A, from the latest approved atrial event detected plus the following A-V interval.

Operation of this known heart stimulator, when the spontaneous atrial heart rate is faster than the fastest synchronous ventricular stimulation rate, causes certain problems. Every time Wenckebach blocking occurs, the following ventricular stimulation pulse is displaced. This results in irregular stimulation of the ventricle during the period in which the atrial pulse rate is faster than the fastest synchronous rate. The pacemaker patient may find this uncomfortable.

Moreover, an increased interval between atrial and ventricular events gives the atrium the time to biologically repolarize before the ventricular stimulation pulse is emitted. As a result, the ventricular stimulation pulse could be conducted to the atrium and stimulate an atrial event. Conduction time is normally longer than the atrial refractory period, so the heart stimulator would then interpret this event as an approved spontaneous atrial event. The heart stimulator could then become unable to exit a loop in which conducted atrial events initiate ventricular stimulation pulses. This is referred to as pacemaker mediated tachycardia, PMT.

Another risk with an excessively long interval between an atrial event and the next ventricular stimulation pulse is that the next spontaneous atrial event could occur at the same time as, or immediately after, the ventricular stimulation pulse. The ventricle in this situation is in a contracted state, and pressure in the ventricle keeps the heart valves between the atrium and the ventricle closed. When the atrium contracts, blood in the atrium will be pumped in the wrong direction, i.e., out of the atrium into the vascular system. This phenomenon is known as the pacemaker syndrome. In addition to being unpleasant to the patient, the process impairs cardiac function. Reflux of blood is impaired during the next heart cycle, the atrium's pumping effect is degraded, and the autonomic nervous system could interpret the retrograde pressure wave as excessively high blood pressure. The body may then react to generate drop in blood pressure leading to fatigue, reduced exercise capacity, dizziness and nausea in the patient. At worst, the drop in blood pressure could be severe enough to cause the patient to faint.

SUMMARY OF THE INVENTION

It is an object of the present invention to provide a heart stimulator and a heart stimulating method which achieves more uniform stimulation of the ventricle when atrial activity is high.

It is also an object of the invention to achieve a heart stimulator and method which prevent the development of PMT and pacemaker syndrome.

The above objects are achieved in a heart stimulator in accordance with the principles of the present invention, having respective atrial and ventricular stimulators (pulse generators) and event detectors, and a control unit, wherein the control unit imposes an extra atrial stimulation pulse at a second predetermined atrioventricular interval before the next ventricular stimulation pulse if the interval between the most recently detected atrial event and the next ventricular stimulation pulse exceeds a predetermined threshold value.

This limits the interval between an atrial event and the next ventricular stimulation pulse, minimizing the risk of PMT or pacemaker syndrome, since the extra atrial stimulation pulse keeps any spontaneous atrial event from occurring before the atrium has repolarized. The extra atrial stimulation pulse also makes an additional contribution to the filling of the ventricle with blood. Since the atrium's spontaneous depolarization occurs with great regularity and the atrial stimulation pulse zeroes, so to speak, the biological timer of the natural interval between two spontaneous atrial events, the interval elapsing between an atrial event and the next ventricular stimulation pulse will again start increasing until it becomes so long than an extra atrial stimulation pulse is emitted. Stimulation of the ventricle thereby becomes more uniform, since Wenckebach blocking only occurs when the atrial heart rate is so fast that the interval between an atrial event and the next ventricular stimulation pulse does not have time to exceed the threshold value before an atrial event occurs during the atrial refractory period. At such a fast atrial rate, however, the next spontaneous atrial event generally occurs before the minimum synchronous interval elapses, and the ventricle's stimulation rate is kept relatively constant. The second atrioventricular interval can be shorter than the first A-V interval, since the primary task of the extra atrial stimulation pulse is to prevent spontaneous atrial events and conduction from the ventricle. The second A-V interval can even have the same duration as the first interval.

In this context, preferably the control unit inhibits the extra atrial stimulation pulse when an atrial event is detected after the most recently detected atrial event and before the minimum synchronous interval has elapsed, and the control unit imposes the first atrioventricular interval after the detected atrial event. The ventricular pulse generator then emits the ventricular stimulation pulse, either after expiration of the first atrioventricular interval or after expiration of the minimum synchronous interval, depending on which interval expires last.

There is no reason to emit an extra atrial stimulation pulse unless the interval between a spontaneous atrial event and the next ventricular stimulation pulse is greater than the threshold value. The extra atrial stimulation pulse is therefore inhibited if another spontaneous atrial event is detected before the extra atrial stimulation pulse is emitted.

The threshold value is preferably selected to consist of an interval corresponding to the atrium's biological refractory period, preferably between 250 and 400 ms.

In a further embodiment of the heart stimulator and method in accordance with the invention, the control unit measures the time elapsing from the latest stimulated or spontaneous ventricular event to the next sensed atrial event and compares this measured time to the minimum synchronous interval minus the threshold value to ascertain whether the interval between the latest atrial event sensed and the next ventricular stimulation pulse exceeds the threshold value. If the timed interval is less than the minimum synchronous interval minus the threshold value, the control unit determines whether the interval exceeds the threshold value.

Since the minimum synchronous interval starts with a ventricular event, the remaining part of the minimum synchronous interval can be determined by measurement of the time elapsing from the ventricular event to the next atrial event. An extra atrial stimulation pulse is emitted if the time exceeds the threshold value. Since both the minimum synchronous interval and the threshold value are programmed in the control unit of the heart stimulator, the difference between these two parameters can be established. If the measured time is less than this difference, the time remaining in the minimum synchronous interval is greater than the threshold value.

Alternatively, the control unit can, in determining whether the interval exceeds the threshold value, sense the sequence of the minimum synchronous interval and prolong the first atrioventricular interval if the first atrioventricular interval expires before the minimum synchronous interval. The prolongation of the first atrioventricular interval is selected so that the interval exceeds the threshold value if the minimum synchronous interval has not elapsed when the prolonged atrioventricular interval expires. The control unit imposes, if the interval exceeds the threshold value, a ventriculoatrial interval after whose expiration the atrial pulse generator emits the extra atrial stimulation pulse, the ventricular pulse generator then emitting the ventricular stimulation pulse after the second atrioventricular interval expires.

By determining an appropriate prolongation of the atrioventricular interval, the heart stimulator can decide when emission of an extra atrial stimulation pulse is suitable if the minimum synchronous interval has not expired when the prolonged A-V refractory period expires. During the ventriculoatrial interval, both the atrium and the ventricle are sensed after spontaneous events. It should be noted that the second atrioventricular interval can be as long as the first atrioventricular interval. The interval can either be set by a function in the heart stimulator or programmed by a physician.

In conjunction with the alternative embodiment, preferably the control unit controls the ventricular pulse generator so that it emits the ventricular stimulation pulse in conjunction with the expiration of the minimum synchronous interval, if the minimum synchronous interval expires before the prolonged atrioventricular interval expires. This results in a more uniform ventricular stimulation rate, since stimulation occurs at the fastest synchronous rate, except when the prolonged atrioventricular interval expires before the minimum synchronous interval.

In another version of the heart stimulator according to the alternative embodiment, the control unit sets the duration of the ventriculoatrial interval by calculating a first interval corresponding to the atrium's biological refractory period minus the sum of the first atrioventricular interval and the prolongation of the first atrioventricular interval and a second interval, corresponding to the minimum synchronous interval, and minus the sum of the time elapsing from the latest ventricular event to the next sensed atrial event, the first atrioventricular interval, the prolongation of the first atrioventricular interval and the second atrioventricular interval. The control unit then compares the first interval with the second interval and sets the length of the ventriculoatrial interval at the longest of the two calculated intervals.

Two conditions must be met before the extra atrial stimulation pulse is emitted. First, the atrium must not be stimulated too soon after the immediately preceding atrial event, especially not in the atrium's biological refractory period. Therefore, because of this first condition, the ventriculoatrial interval must not be shorter than the atrium's biological refractory period less the sum of the first atrioventricular interval and the prolongation of the first atrioventricular interval. Since the atrium's biological refractory period can vary from one individual to another and can even vary in the same individual, a suitable period is set in which the atrium reliably has time to repolarize, e.g. 300 ms. The second condition is that a ventricular stimulation pulse must not be emitted until the minimum synchronous interval has elapsed. Because of the second condition, therefore, the ventriculoatrial interval must not be shorter than the minimum synchronous interval less the sum of the time elapsing from the latest ventricular event to the next sensed atrial event, the first atrioventricular interval, the prolongation of the first atrioventricular interval and the second atrioventricular interval. The extra atrial stimulation pulse is emitted, because of the second condition, before the minimum synchronous interval has elapsed, i.e. after an interval consisting of the second atrioventricular interval before expiration of the minimum synchronous interval.

DESCRIPTION OF THE DRAWINGS

FIG. I is a schematic block diagram of a heart stimulator constructed in accordance with the principles of the present invention and operating according to the inventive method.

FIG. 4 shows in a time diagram a number of heart cycles illustrating the functioning of the heart stimulator of FIG. 1 over a second sequence of events.

DESCRIPTION OF THE PREFERRED EMBODIMENTS

Figure 2A:
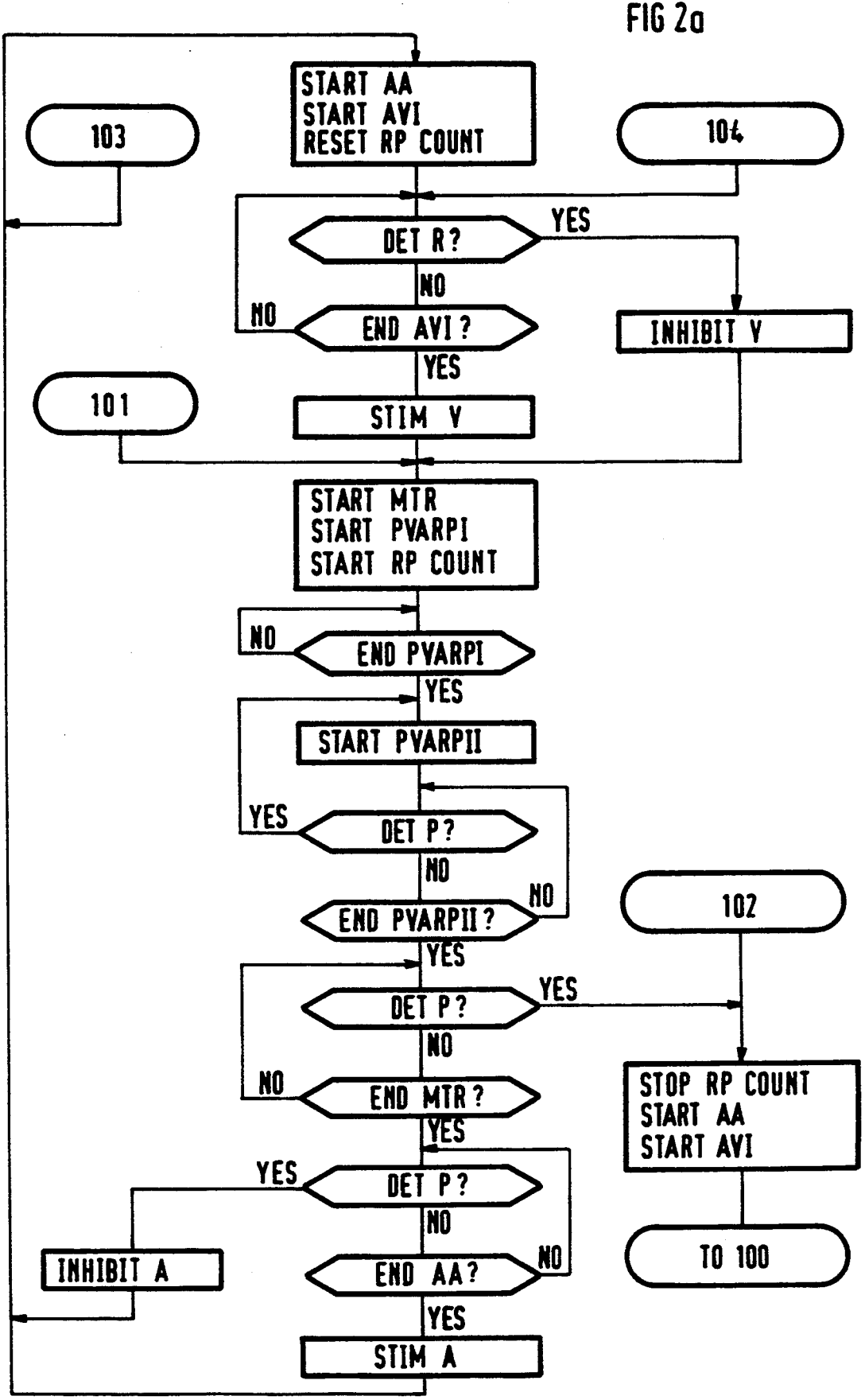
FIGS. 2a and 2b in combination show a flowchart for functions which can be performed with the heart stimulator of FIG. 1.

The heart stimulator of FIG. 1 is in the form of a bipolar dual chamber pacemaker 1. The pacemaker I is connected to the atrium in a heart 2 via a first tip electrode 3 and a first ring electrode 4 and to the ventricle of the heart 2 via a second tip electrode 5 and a second ring electrode 6. An atrial pulse generator 7 in the pacemaker I is respectively connected by a first electrode conductor 8 and a second electrode conductor 9 to the first ring electrode 4 and the first tip electrode 3 respectively so as to deliver atrial stimulation pulses. An atrial detector unit 10 for sensing atrial events is connected in parallel with the atrial pulse generator 7.

In a corresponding manner, a ventricular pulse generator 11 is respectively connected to the second ring electrode 6 and the second tip electrode 5 by a third electrode conductor 12 and a fourth electrode conductor 13, for emitting ventricular stimulation pulses. A ventricular detector unit 14 for sensing ventricular events is connected in parallel with the ventricular pulse generator 11.

The pulse generators 7 and 11 are controlled by a control unit 15 which controls the emission of stimulation pulses with respect to timing, amplitude and duration. The control unit 15 also controls the detector units 10 and 14 and receives information about sensed events therefrom.

A physician, using an external programming unit 16, can check and change program parameters in the control unit 15. Communication between the control unit 15 and the programming unit 16 is established via a telemetry unit 17, connected to the control unit 15, which transmits/receives information to/from the programming unit 16.

The pacemaker 1 contains an activity sensor 18 for sensing the pacemaker patient's physical activity, enabling the control unit 15 to adapt the stimulation rate to the patient's level of physical activity.

The pacemaker 1 operates with an inhibitory function. This means that no stimulation pulses are supplied as long as the heart 2 spontaneously functions at an adequate rate. If, e.g., only the atrium functions spontaneously at an adequate rate, the ventricular pulse generator emits a ventricular stimulation pulse after expiration of an atrioventricular interval, the A-V interval, which starts when an atrial event is sensed. To keep the ventricle from being stimulated at an excessively fast rate when the atrium's spontaneous pulse rate is too fast, emission of ventricular stimulation pulses is limited by a maximum synchronous stimulation rate, MTR. However, "MTR" will henceforth designate the minimum synchronous interval corresponding to the maximum synchronous rate. MTR is programmable and set by a physician.

Figure 2B:
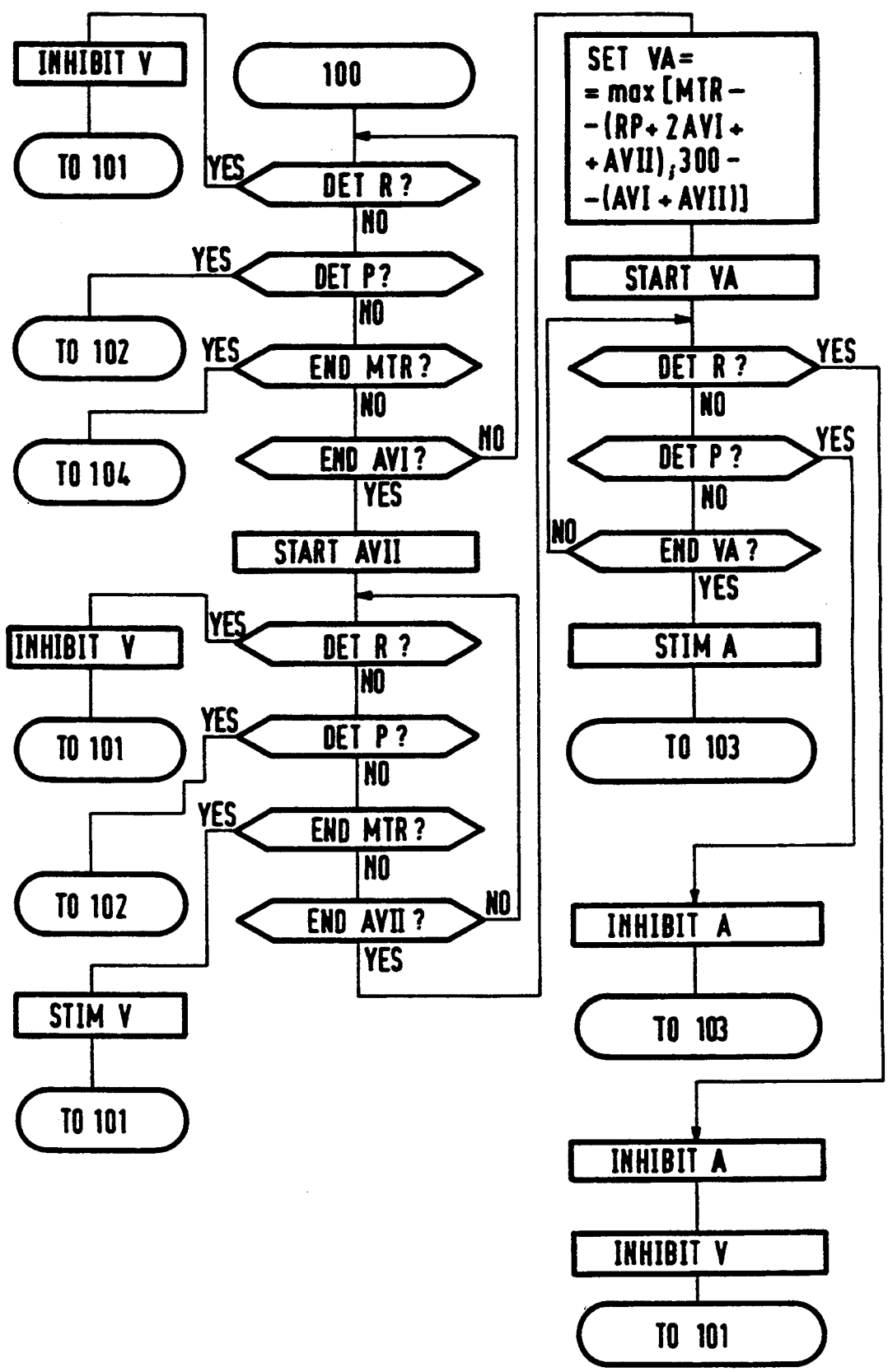

A flowchart is shown in FIGS. 2a and 2b which schematically describes functions the pacemaker 1 can perform to optimize the pacemaker's operation when the atrium's spontaneous pulse rate is faster than the MTR. In the flow chart, A designates atrial events in general, P spontaneous atrial events, V ventricular events in general and R spontaneous ventricular events. AA designates a basic interval for the atrium at which the pacemaker 1 stimulates the atrium if the atrium's spontaneous pulse rate slows too much. The basic interval AA can be controlled by the patient's level of physical activity when the activity sensor 18 is activated by the control unit 15. RP designates the interval elapsing between a ventricular event (spontaneous or stimulated) and the next atrial event. Other designations will be explained as introduced.

The function block at the top in FIG. 2a designates the sequence in a spontaneous or stimulated atrial event. The AA interval and a first A-V interval (AVI) are started, and timing of the RP interval is zeroed. The ventricle is sensed in the next block (DET R?). If a ventricular event is detected (exit YES block DET R?), emission of the ventricular stimulation pulse is inhibited (INHIBIT V), and the pacemaker 1 continues operation. If no ventricular event is sensed (exit No block DET R?), expiration of the AVI interval (exit YES block END AVI?) is awaited before a ventricular stimulation pulse is emitted (STIM V).

The MTR interval, timing of the RP interval and an absolute atrial refractory period, PVARPI, start after a ventricular event (stimulated or spontaneous). The atrial detector unit 10 is inactive during PVARPI, since the ventricular stimulation pulse causes noise making it very difficult to separate signals generated by an atrial event. After expiration of the atrial refractory period PVARPI, a relative atrial refractory period PVARPII starts (START PVARPII). The atrial detector unit 10 is activated during the PVARPII period in order to sense the atrium. However, detections during the PVARPII period are interpreted as noise from the ventricular event and only cause the PVARPII period to restart. The PVARPII period is thus continually restarted until no detections occur during the PVARPII period (exit NO block DET P? and exit YES block END PVARPII?).

The atrial detector unit 10 continues sensing the atrium (DET P?) after the PVARPII period elapses. If no atrial events are sensed before the MTR interval has expired (exit YES block END MTR?), the pacemaker 1 switches to the next block sequence. The atrium still senses (DET P?) while awaiting expiration of the AA interval (END AA?). If an atrial event is detected (exit YES block DET P?), emission of the atrial stimulation pulse is inhibited (INHIBIT A), and the functional sequence continues according to the first block. This is also the case when the AA interval expires (exit YES block END AA?) without any event being detected in the atrium, whereupon a stimulation pulse is 5 first emitted in the atrium (STIM A) before the functional sequence continues according to the first block.

If an atrial event is detected before the MTR interval expires (exit NO block END MTR? and exit YES block DET P?), timing of the RP interval is stopped while the AA interval simultaneously restarts and the AVI interval starts. The functional sequence continues according to FIG. 2b. The ventricle is then sensed (DET R?) in the same way as previously described. If a ventricular event is sensed (exit YES block DET R?) before the AVI interval or the MTR interval expires, emission of the ventricular stimulation pulse is inhibited (INHIBIT V), and the sequence continues according to block 101 in FIG. 2a. In addition, the atrium continues to be sensed (DET P?). This is to prevent emission of asynchronous atrial stimulation pulses which could be dangerous. If an atrial event is sensed (exit YES block DET P?) before the MTR interval expires, the AA and AVI intervals restart according to block 102 in FIG. 2a. If the MTR interval expires before the AVI interval (exit YES block END MTR?), the ventricle is sensed during the rest of the AVI interval according to block 104 in FIG. 2a, and the ventricular stimulation pulse is inhibited (INHIBIT V) or emitted (STIM V), depending on whether a ventricular event is detected or not. If the AVI interval expires before the MTR interval (exit YES block END AVI?), the sequence continues according to the next block sequence in FIG. 2b.

Prolongation of the AVI interval starts (start AVII), and the atrium and ventricle are sensed. An atrial event (exit YES block DET P?) causes the AA and AVI intervals to restart according to block 102 in FIG. 2a. A ventricular event (exit YES block DET R?) causes the sequence to continue with inhibition of the ventricular stimulation pulse (INHIBIT V), the sequence then continuing according to block 101 in FIG. 2a. If the MTR interval expires before the AVII interval (exit YES block END MTR?), a ventricular stimulation pulse (STIM V) is emitted, the sequence then continuing at block 102 in FIG. 2a. If the AVII interval expires before the MTR interval (exit YES block END AVII?), the interval between the latest atrial event to emission of the ventricular stimulation pulse will be so long that the atrium biologically recovers from the most recent atrial event, i.e. heart tissue in the atrium repolarizes. There is then a risk of a ventricular stimulation pulse being conducted to the atrium, causing a depolarization in the atrium which is interpreted by the atrial detector unit 10 as a spontaneous atrial event. This means that the pacemaker could become unable to exit a loop in which conducted atrial events cause the emission of ventricular stimulation pulses, i.e. pacemaker mediated tachycardia (PMT). Another problem which could arise is the occurrence of spontaneous atrial event immediately after the ventricular stimulation pulse. The ventricle would then be in a contracted state, and pressure in the ventricle would keep the heart valves between the atrium and the ventricle closed. When the atrium contracts in this situation, blood in the atrium can only be pumped backwards into the vascular system. In addition to being unpleasant to the patient, this impairs the return of blood to the heart during its bloodfilling phase, and the atrium's pumping effect is impaired. In addition, a retrograde pressure wave in the vascular system can act on the autonomic nervous system and be interpreted as a rise in blood pressure. The nervous system then strives to reduce blood pressure, a process which could cause the patient to faint.

According to the functional diagram, therefore, a ventriculoatrial interval, i.e. the VA interval, is set after whose expiration an atrial and a ventricular stimulation pulse are emitted in sequence. The extra atrial stimulation pulse prevents reconduction after the ventricular stimulation pulse and also prevents spontaneous atrial events until the atrium has again repolarized. The VA interval normally designates an interval between a ventricular event to the next occurrence of an atrial stimulation pulse but is still used in conjunction 5 with this function example, since it designates the time elapsing to a subsequent atrial stimulation pulse. The duration set for the VA interval (block SET VA = ..., is affected by two conditions. The first is that the ventricular stimulation pulse must not be emitted until the MTR interval has elapsed. A preceding extra atrial stimulation pulse can therefore only be emitted, at the earliest, after a period of time corresponding to the A-V interval, before the MTR interval expires. In this example, the AVI interval was used, but another A-V interval can be used for the extra atrial stimulation pulse. To satisfy the first condition, the VA interval must be longer than the MTR interval less the sum of the RP interval, two AVI intervals and the AVII interval. The second condition is that the atrium must not be stimulated too soon after a preceding atrial event, since this could induce atrial fibrillation. This time can normally be set at 300 ms. Therefore, to satisfy the second condition, the VA interval must be at least 300 ms less the sum of the AVI and AVII intervals. The condition resulting in the longest interval therefore governs the length of the VA interval.

When the length of the VA interval has been set, this interval starts (start VA), and both the ventricle (DET R?) and the atrium (DET P?) are then sensed after spontaneous events. A detected ventricular event (exit YES block DET R?) causes inhibition of both the atrial and ventricular stimulation pulses at block 101 in FIG. 2a, whereas a detected atrial event causes inhibition of the atrial stimulation pulse (INHIBIT A), and the sequence continues at block 103 in FIG. 2a, i.e. the first function block. If no events are detected before the VA interval expires (exit YES block END VA?), the extra atrial 0 stimulation pulse is emitted, and the sequence then continues at block 103 in FIG. 2a.

Figure 3:
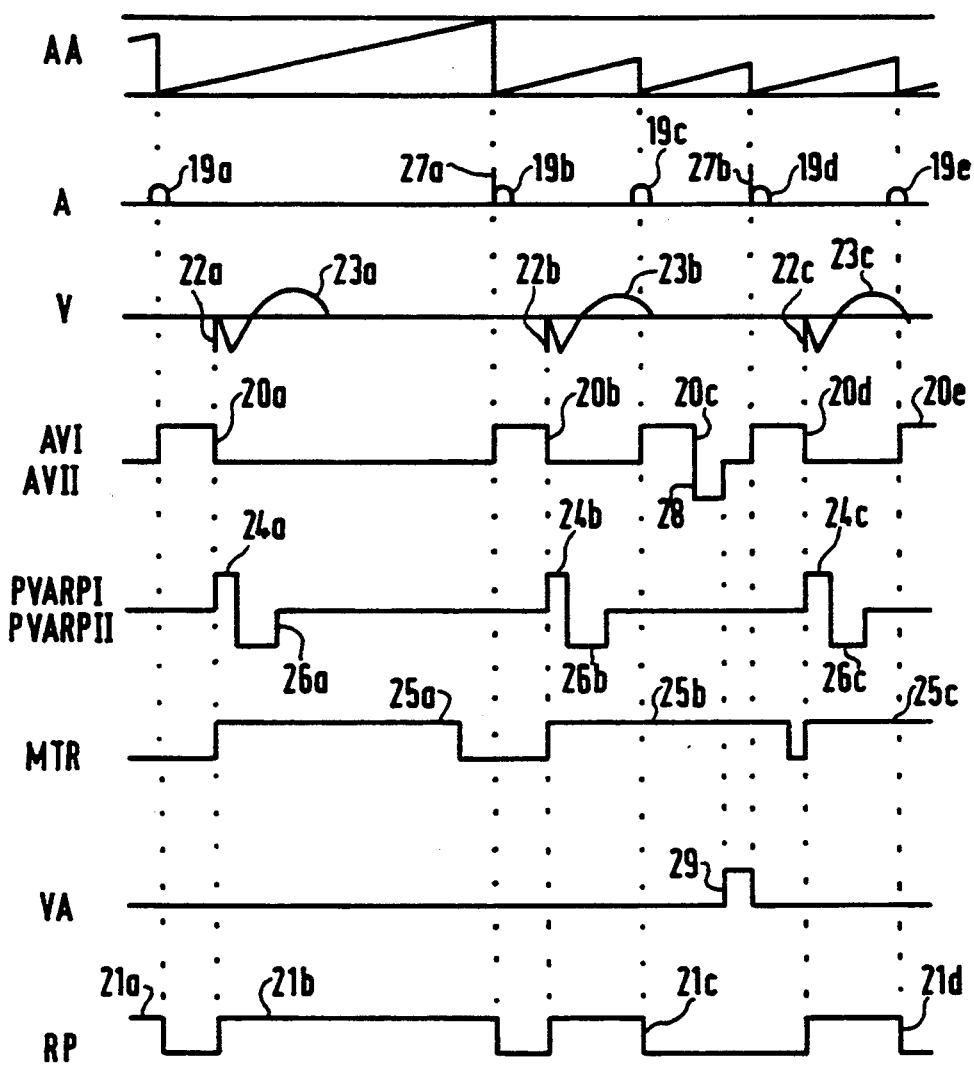
FIG. 3 shows, in a time diagram, a number of heart cycles illustrating functioning of the heart stimulator of FIG. 1 over a first sequence of events.

Two time diagrams, FIGS. 3 and 4, illustrate the function described in conjunction with the flowchart in FIGS. 2a and 2b. FIGS. 3 and 4 show the following parameters and variables in this order: the A-A interval, events in the atrium (A), events in the ventricle (V), the AVI interval, the AVII interval, the PVARPI period, the PVARPII period, the MTR interval, the VA interval and the RP interval.

In FIG. 3, the diagram begins with a spontaneous atrial event 19a. The atrial event 19a zeroes and restart the timing of the AA interval, starts an AVI interval 20a and stops timing of an RP interval 21a. When the AVI interval 20a expires without any other events occurring, a ventricular stimulation pulse 22a is emitted which results in a stimulated ventricular event 23a. At the same time, a PVARPI period 24a starts, during which there is no sensing of atrial activity, an MTR interval 25a and timing of the next RP interval 21b. When PVARPI 24a expires, a PVARPII period 26a starts, during which the atrium is sensed. However, detections are interpreted as noise. After this, nothing happens until the AA interval expires, and an atrial stimulation pulse 27a is emitted, stimulating an atrial event 19b. At the same time as the atrial stimulation pulse 27a is emitted, timing of the AA interval, as well as the AVI interval, restarts. In addition, timing of the RP interval 21b is interrupted.

After the AVI interval 20b expires, a ventricular stimulation pulse 22b is emitted at the same time as a new PVARPI period 24b, a new MTR interval 25b and renewed timing of an RP interval 21c start. The ventricular stimulation pulse 22b results in a ventricular event 23b. When the PVARPI period 24b expires, a PVARPII period 26b starts during which no events occur. Before the AA interval expires, an atrial event 19c is now detected which results in the start of a new AA interval and an AVI interval 20c. The MTR interval 25b has not yet expired at the time the AVI interval 20c expires, and the control unit 15 then prolongs the AVI interval 20c, i.e. to create an AVII interval 28. Since the MTR interval 25b has not expired at the time the AVII interval 28 expires, the control unit 15 imposes a VA interval 29 whose duration is established as described in conjunction with the flow chart in FIGS. 2a and 2b.

When the VA interval 29 expires, an atrial stimulation pulse 27b is emitted at the same time as timing of the AA interval restarts, and a new AVI interval 20d starts. The atrial stimulation pulse 27b stimulates an atrial event 19d. In this instance, the duration of the VA interval 29 is governed by the condition for atrial stimulation, so the MTR interval 25b expires before the AVI interval 20d expires. A ventricular stimulation pulse 22c is emitted and stimulates a ventricular event 23c. At the same time, a PVARPI period 24c, an MTR interval 25c and timing of an RP interval 21d start. A PVARPII period 26c follows expiration of the PVARPI period 24c, and the PVARPII 26c period expires without any event occurring.

A spontaneous atrial event 19e is detected and restarts timing of the AA interval, starts an AVI interval 20e and stops timing of the RP interval 21d. The sequence continues as described above until the spontaneous atrial pulse rate is again faster than the rate corresponding to the MTR interval. Since depolarization of the atrium is a very regular process and stimulation of the atrium zeroes the atrium's biological depolarization period, there is no retrograde migration of atrial events until they occur during the PVARPII period in this case. Stimulation of the ventricle is therefore very uniform and largely coincides with the MTR period.

The diagram in FIG. 4 starts in the same way as the diagram in FIG. 3, i.e. with an atrial event 30a which starts the timing of an AA interval and an AVI interval 31a and stops timing of an RP interval 32a. When the AVI interval 31a expires, a ventricular stimulation pulse 33a is emitted which results in a stimulated ventricular event 34a. At the same time as the ventricular stimulation pulse 33a is emitted, a PVARPI period 35a, an MTR interval 36a and timing of an RP interval 32b start. The PVARPI period 35a is followed by a PVARPII period 37a.

No events occur during the rest of the AA interval, and an atrial stimulation pulse 38, resulting in a stimulated atrial event 30b, is emitted when the AA interval expires. At the same time as the atrial stimulation pulse 38 is emitted, the timing of a new AA interval and an AVI interval 31b starts. Timing of the RP interval 32b also stops. When the AVI interval 31b expires, a ventricular stimulation pulse 33b is emitted at the same time as a PVARPI period 35b, an MTR interval 36b and timing of an RP interval 32c start. The ventricular stimulation pulse 33b results in a stimulated ventricular event 34b. A PVARPII period 37b starts after a PVARPI period 35b expires. During the PVARPII period 37b, the atrial detector unit 10 detects an atrial event 30c. However, the control unit 15 is programmed to interpret detection during the PVARPII period as noise, and a restart of the PVARPII period 37b is thus the only effect of this detection. No additional events are now detected, and the PVARPII period 37b expires.

An approved atrial event is then sensed, causing timing of the AA interval to restart, the AVI interval 31c to start and timing of the RP interval 32c to stop. The MTR interval 36b has not expired when the AVI interval 31c expires, so no ventricular stimulation pulse is emitted. An AVII interval 39a starts instead. The MTR interval 36b expires before the AVII interval 39a expires, and a ventricular stimulation pulse 33c expires at the same time as a PVARPI period 35c and an MTR interval 36c start. Renewed timing of an RP interval 32d also starts. A stimulated ventricular event 34c follows the ventricular stimulation pulse 33c.

A PVARPII period 37c, during which an atrial event 30e occurs, starts after expiration of the PVARPI period 35a. As noted 5 above, this only results in the continual restart of the PVARPI period 37c until the period can expire without any detection occurring in the interval.

An approved atrial event 30f starts the timing of an AA interval and an AVI interval 31d. In addition, the timing of 5 the RP interval 32d stops. The MTR interval 36c has not expired when the AVI interval 31d expires, and no stimulation pulse is emitted. An AVII interval 39b starts instead. The MTR interval 36c has still not expired when the AVII interval 39b expires, and the control unit 15 determines a VA interval 40 and 0 imposes this VA interval. Before the VA interval 40 expires, an atrial event 30g is detected, and the extra atrial stimulation pulse is inhibited. Timing of a new AA interval and an AVI interval 31e start at the same time. The sequence then continues in the corresponding way until there is a change in the pulse rate for 5 the atrial events.

The function according to the invention, i.e. to emit an extra atrial stimulation pulse when the interval between an atrial event and the next ventricular stimulation pulse becomes too long, operates just as efficaciously in instances when the heart stimulator works at a preprogrammed atrial stimulation rate or according to the physical activity sensed by the activity sensor. In spontaneous activity, the atrial stimulation pulse is then inhibited normally, and the ventricular stimulation pulse is emitted after the expiration of an A-V interval following the inhibited atrial stimulation pulse. If, as noted above, the interval is too long, an additional atrial stimulation pulse is emitted and the ventricular stimulation pulse is emitted after the AA interval.

Although modifications and changes may be suggested by those skilled in the art, it is the intention of the inventors to embody within the patent warranted hereon all changes and modifications as reasonably and properly come within the scope of their contribution to the art.

I claim as my invention:

1. A method for electrically stimulating a heart comprising the steps of:
   detecting spontaneous and stimulated cardiac events in each of the atrium and the ventricle of a heart;
   delivering a series of atrial stimulation pulses to said atrium at a programmable basic interval;
   inhibiting delivery of an atrial stimulation pulse if a spontaneous atrial event is detected during said basic interval;
   delivering a ventricular stimulation pulse after expiration of a first atrioventricular interval following each inhibited or stimulated atrial pulse or a spontaneous atrial event, or after expiration of a minimum synchronous interval following a stimulated or spontaneous ventricular event, dependent on which of said first atrial ventricular interval or said minimum synchronous interval elapses last; and
   delivering an extra atrial stimulation pulse at a second predetermined atrioventricular interval before a next ventricular stimulation pulse if an interval between a most recently detected atrial event and said next ventricular stimulation pulse exceeds a predetermined threshold value.

2. A method as claimed in claim 1 comprising the additional steps of:
   inhibiting delivering of said extra atrial stimulation pulse if an atrial event is detected after said most recently detected atrial event and before the expiration of said minimum synchronous interval;
   starting said first atrioventricular interval after detection of said atrial event after said most recently detected atrial event; and
   delivering a ventricular stimulation pulse either after the expiration of said first atrioventricular interval or after the expiration of said minimum synchronous interval, dependent on which of said first atrioventricular interval or said minimum synchronous interval expires last.

3. A method as claimed in claim 1 comprising the additional step of:
   setting said predetermined threshold value to a value corresponding to the biological refractory period of the atrium.

4. A method as claimed in claim 1 comprising the additional step of:
   setting said predetermined threshold value to a value between 250 and 400 ms.

5. A method as claimed in claim 1 comprising the additional steps of:
   measuring a time elapsing from a most recent stimulated or spontaneous ventricular event to a next sensed atrial event, and thereby obtaining a measured time; and
   comparing said measured time to said minimum synchronous interval minus said threshold value to determine whether said interval between said latest sensed atrial event and said next ventricular stimulation pulse exceeds said threshold value, said interval exceeding said threshold value if said measured time is less than said minimum synchronous interval minus said threshold value.

6. A method as claimed in claim 1 comprising the additional steps of:
   determining whether said interval between said most recently detected atrial event and said next ventricular stimulation pulse exceeds said predetermined threshold value;
   prolonging said first atrioventricular interval if said first atrioventricular interval expires before said minimum synchronous interval, and selecting the prolongation of said first atrioventricular interval so that the prolonged, first atrioventricular interval exceeds said threshold value if said minimum synchronous interval has not elapsed when said prolonged, first atrioventricular interval elapses; and
   if said interval between said most recently detected atrial event and said next ventricular stimulation pulses exceeds said predetermined threshold value, starting a ventriculoatrial interval and delivering said extra atrial stimulation pulse after the expiration of said ventriculoatrial interval, and thereafter delivering a ventricular stimulation pulse upon expiration of said second atrioventricular interval.

7. A method as claimed in claim 6 comprising the additional step of:
   delivering said ventricular stimulation pulse upon the expiration of said minimum synchronous interval if said minimum synchronous interval expires before said prolonged, first atrioventricular interval expires.

8. A method as claimed in claim 7 comprising the additional steps, for setting a duration of said ventriculoatrial interval, of:
   calculating a first interval corresponding to a biological refractory period of the atrium minus the sum of said first atrioventricular interval and said prolonged, first atrioventricular interval;
   calculating a second interval corresponding to said minimum synchronous interval minus the sum of a time elapsing from a latest ventricular event to a next sensed atrial event, said first atrioventricular interval, said prolonged, first atrioventricular interval, and said second atrioventricular interval; and
   comparing said first interval with said second interval and setting said duration of said ventriculoatrial interval to the longest of said first and second intervals.

9. An apparatus for electrically stimulating a heart comprising:
   means for detecting spontaneous and stimulated cardiac events in each of the atrium and the ventricle of a heart;
   means for delivering a series of atrial stimulation pulses to said atrium at a programmable basic interval;
   a control unit including means for inhibiting delivery of an atrial stimulation pulse if a spontaneous atrial event is detected during said basic interval;
   said control unit further including means for causing delivery of a ventricular stimulation pulse after expiration of a first atrioventricular interval following each inhibited or stimulated atrial pulse or a spontaneous atrial event, or after expiration of a minimum synchronous interval following a stimulated or spontaneous ventricular event, dependent on which of said first atrial ventricular interval or said minimum synchronous interval elapses last; and said control unit further including means for causing delivery of an extra atrial stimulation pulse at a second predetermined atrioventricular interval before a next ventricular stimulation pulse if an interval between a most recently detected atrial event and said next ventricular stimulation pulse exceeds a predetermined threshold value.

10. An apparatus as claimed in claim 9 wherein said control unit further includes:

means for inhibiting delivery of said extra atrial stimulation pulse if an atrial event is detected after said most recently detected atrial event and before the expiration of said minimum synchronous interval;

means for starting said first atrioventricular interval after detection of said atrial event after said most recently detected atrial event; and means for causing delivery of a ventricular stimulation pulse either after the expiration of said first atrioventricular interval or after the expiration of said minimum synchronous interval, dependent on which of said first atrioventricular interval or said minimum synchronous interval expires last.

11. An apparatus as claimed in claim 9 wherein said control unit further includes:

means for setting said predetermined threshold value to a value corresponding to the biological refractory period of the atrium.

12. An apparatus as claimed in claim 9 wherein said control unit further includes:

means for setting said predetermined threshold value to a value between 250 and 400 ms.

13. An apparatus as claimed in claim 9 wherein said control unit further includes:

means for measuring a time elapsing from a most recent stimulated or spontaneous ventricular event to a next sensed atrial event, and thereby obtaining a measured time; and means for comparing said measured time to said minimum synchronous interval minus said threshold value to determine whether said interval between said latest sensed atrial event and said next ventricular stimulation pulse exceeds said threshold value, said interval exceeding said threshold value if said measured time is less than said minimum synchronous interval minus said threshold value.

14. An apparatus as claimed in claim 9 wherein said control unit further includes:

means determining whether said interval between said most recently detected atrial event and said next ventricular stimulation pulse exceeds said predetermined threshold value;

means, if said first atrioventricular interval expires before said minimum synchronous interval, for prolonging said first atrioventricular interval so that the prolonged, first atrioventricular interval exceeds said threshold value if said minimum synchronous interval has not elapsed when said prolonged, first atrioventricular interval elapses; and means, if said interval between said most recently detected atrial event and said next ventricular stimulation pulses exceeds said predetermined threshold value, for starting a ventriculoatrial interval and delivering said extra atrial stimulation pulse after the expiration of said ventricular atrial interval, and for thereafter causing delivery of a ventricular stimulation pulse upon expiration of said second atrioventricular interval.

15. An apparatus as claimed in claim 14 wherein said control unit further includes:

means for causing delivery of said ventricular stimulation pulse upon the expiration of said minimum synchronous interval if said minimum synchronous interval expires before said prolonged, first atrioventricular interval expires.

16. An apparatus as claimed in claim 15 wherein said control unit further includes means for setting a duration of said ventriculoatrial interval comprising:

means for calculating a first interval corresponding to a biological refractory period of the atrium minus the sum of said first atrioventricular interval and said prolonged, first atrioventricular interval;

means for calculating a second interval corresponding to said minimum synchronous interval minus the sum of a time elapsing from a latest ventricular event to a next sensed atrial event, said first atrioventricular interval, said prolonged, first atrioventricular interval, and said second atrioventricular interval; and means for comparing said first interval with said second interval and for setting said duration of said ventriculoatrial interval to the longest of said first and second intervals.

* * * * *